US011090178B1

(12) United States Patent
Moody et al.

(10) Patent No.: US 11,090,178 B1
(45) Date of Patent: Aug. 17, 2021

(54) ADAPTIVE DEVICE FOR A HAND (71) Applicants: Jane Malone Moody, San Antonio, TX (US); Joe Marshall Moody, III, San Antonio, TX (US)

(72) Inventors: Jane Malone Moody, San Antonio, TX (US); Joe Marshall Moody, III, San Antonio, TX (US)

( * ) Notice: Subject to any disclaimer, the term of this patent is extended or adjusted under 35 U.S.C. 154(b) by 22 days.

(21) Appl. No.: 16/668,354

(22) Filed: Oct. 30, 2019

(51) Int. Cl.
*A61F 4/00* (2006.01)
*B65D 25/10* (2006.01)
*A61F 5/01* (2006.01)

(52) U.S. Cl.
CPC .............. *A61F 4/00* (2013.01); *A61F 5/013* (2013.01); *B65D 25/108* (2013.01); *A61F 5/0118* (2013.01)

(58) Field of Classification Search
CPC .......... A61F 4/00; A61F 5/013; A61F 5/0118; A61F 2/42; A61F 2/4241; A61F 2/4261; A61F 2/4606; A61F 2/58; A61F 2/583; A61F 2/585; A61F 5/05866; A61F 5/04; A61F 5/05; A61F 2007/0035; A61F 13/107; A61F 2/588; A61F 2007/0036; A61F 13/10; A61F 13/104; A61F 5/37; B65D 25/108

See application file for complete search history.

(56) References Cited

U.S. PATENT DOCUMENTS

| 3,521,625 A | * | 7/1970 | Mackey | ............... | A61M 5/52 |
| | | | | | 128/877 |
| 3,526,006 A | * | 9/1970 | Beardmore | ......... | A61F 5/05866 |
| | | | | | 623/57 |
| 4,447,912 A | | 5/1984 | Morrow | | |
| 4,511,272 A | * | 4/1985 | Brown | ................... | B43L 15/00 |
| | | | | | 401/48 |
| 4,602,885 A | | 7/1986 | Bischoff et al. | | |
| 4,821,417 A | | 4/1989 | Levine | | |

(Continued)

FOREIGN PATENT DOCUMENTS

DE  4400496 C2  * 11/1997  ............. A61H 39/04

OTHER PUBLICATIONS

"Tactee Kit", https://www.spsco.com/tactee-kit.html [online], retrieved on Sep. 18, 2019 2019.

(Continued)

*Primary Examiner* — Tarla R Patel
(74) *Attorney, Agent, or Firm* — McAfee & Taft, a Professional Corporation (57) ABSTRACT

An adaptive device for a hand for individuals with mobility impairment. The adaptive device comprising a body; wherein the body has a proximal end and a distal end, and wherein the body supports a palm and a wrist when worn by a user. The adaptive device includes two sidewalls extending upward from the body and on opposite sides of the body from each other. At a proximal end of each sidewall, each sidewall includes a slot for receiving a securing member, and wherein the securing member removably secures the hand with the adaptive device when worn by the user. The adaptive device includes a retention member positioned on the body at the distal end and the retention member provides a separation between an index finger and a thumb of the hand, and the retention member removably couples with an interchangeable implement member.

18 Claims, 11 Drawing Sheets

(56) References Cited

U.S. PATENT DOCUMENTS

| | | | |
|---|---|---|---|
| 4,917,517 A | | 4/1990 | Ertz |
| 5,222,986 A | * | 6/1993 | Wright .................... A61F 2/588 |
| | | | 623/64 |
| 5,520,625 A | * | 5/1996 | Malewicz ............. A61F 5/0125 |
| | | | 602/16 |
| 5,597,189 A | | 1/1997 | Barbee, Sr. |
| 6,730,049 B2 | * | 5/2004 | Kalvert ................. A61F 5/0118 |
| | | | 600/545 |
| 7,469,866 B2 | * | 12/2008 | Thompson ................ A61F 4/00 |
| | | | 128/877 |
| 8,840,157 B2 | | 9/2014 | Dempsey et al. |
| 2016/0045336 A1 | | 2/2016 | Cordell et al. |
| 2017/0216078 A1 | | 8/2017 | Rivlin et al. |
| 2021/0077280 A1 | * | 3/2021 | Dechev ..................... A61F 2/70 |

OTHER PUBLICATIONS

"Affordable Multipurpose Prosthetic for People Without Fingers", https://www.instructables.com/id/Affordable-Multipurpose-Prosthetic-for-People-With/ [online] , retreived on Sep. 18, 2019 2019.

* cited by examiner

ADAPTIVE DEVICE FOR A HAND

TECHNICAL FIELD

The present disclosure relates generally to a storage device and an adaptive device for a hand for use by individuals with mobility impairments to improve such individuals' independence.

BACKGROUND

Physically disabling conditions, such as amyotrophic lateral sclerosis (commonly referred to as ALS) and cerebral palsy can cause difficulty or incapability in performing everyday tasks, including writing, eating, and using technology. Limited physical dexterity, particularly in the wrists and hands, significantly contributes to the loss or impairment of motor function.

For example, a diminished capacity to hold an implement, such as a utensil or writing device, between the fingers, or limited strength or mobility of the wrists to move the implement, or the pain associated therewith, can make it difficult or impossible to successfully and independently perform daily tasks, such as self-feeding, writing a letter, or using a stylus. There is a need for effective and comfortable use of ordinary utensils in order to achieve more autonomy and personal fulfillment for those afflicted with mobility impairments.

A poorly fitting adaptive device or other prosthetic can inhibit the user's range of motion and coordination and can cause irritation or discomfort upon attachment or extended use of the device. Contrary to the need for greater autonomy and personal fulfillment, such inadequately or uncomfortably fitting devices can cause ineffective use or even discourage use altogether.

SUMMARY

An adaptive device for a hand comprising a body; wherein the body has a proximal end and a distal end, and wherein the body supports a palm and a wrist when worn by a user. The adaptive device includes two sidewalls extending upward from the body and on opposite sides of the body from each other. At a proximal end of each sidewall, each sidewall includes a slot for receiving a securing member, and wherein the securing member removably secures the hand with the adaptive device when worn by the user. The adaptive device includes a retention member positioned on the body at the distal end and the retention member provides a separation between an index finger and a thumb of the hand, and the retention member removably couples with an interchangeable implement member.

A storage device for holding one or more interchangeable implements for an adaptive device for a hand comprising: a base member and a spacer member positioned on top of the base member. The spacer member having a crenellation top periphery of alternating crenels and merlons; and the storage device including a plurality of guiderails, wherein each guiderail is positioned adjacent to a crenel and on top of a merlon and emanates upward from the top periphery of the spacer member. Wherein guiderails positioned on opposite sides of a shared crenel are a guiderail pair, and a passage is defined between each guiderail in the guiderail pair of the shared crenel.

BRIEF DESCRIPTION OF THE DRAWINGS

FIG. 3A is an axonometric view of an interchangeable implement member and retention member of the adaptive device.
FIG. 3C is a side view of the interchangeable implement member and retention member of the adaptive device of FIG. 3A.
FIG. 3D is another top view of the interchangeable implement member and retention member of the adaptive device with the balls of interchangeable implement member in a retracted position.
FIG. 3E is a top view of another configuration of the connection member of the interchangeable implement member and retention member of the adaptive device.

DETAILED DESCRIPTION

The present disclosure may be understood more readily by reference to this detailed description. For simplicity and clarity of illustration, where appropriate, reference numerals may be repeated among the different figures to indicate corresponding or analogous elements. In addition, numerous specific details are set forth in order to provide a thorough understanding of the various components and configurations of the devices and methods described herein. However, it will be understood by those of ordinary skill in the art that the examples described herein can be practiced without these specific details. In other instances, methods, procedures, and components have not been described in detail so as not to obscure the related relevant feature being described. Also, the description is not to be considered as limiting in scope. The drawings are not necessarily to scale and the proportions of certain parts have been exaggerated to better illustrate details and features of the present disclosure.

The terms of approximation, including, "generally," "substantially," "about," "approximately," and the like, and each of their respective variants and derivatives will be understood to allow for minor variations and/or deviations that do not result in a significant impact thereto. Such terms of approximation should be interpreted according to their ordinary and customary meanings as used in the associated art unless indicated otherwise. Absent a specific definition and absent ordinary and customary usage in the associated art, such terms should be interpreted to be ±2.5% of the base value.

The use of ordinal number terminology (i.e., "first," "second," "third," "fourth," etc.) is for the purpose of differentiating between two or more items and is not meant to imply any sequence or order or importance to one item over another or any order of addition. The term "or combinations thereof" as used herein refers to all permutations and combinations of the listed items preceding the term. The skilled artisan will understand that typically there is no limit on the number of items or terms in any combination, unless otherwise apparent from the context.

As will be used herein, directional terms, such as "above," "below," "upper," "lower," "top," etc. illustrate general points of reference and are used for convenience in referring to the accompanying drawings and descriptions thereof and are not intended to limit the scope of the appended claims.

Standard physiological terminology is used herein to describe the position and orientation of the adaptive device. For ease of readability, the following definitions are intended to be applied throughout this document:

Proximal: Situated near the center of the body or closer to the point of origin of a structure.

Distal: Situated away from the center of the body or furthest point away from the point of origin of a structure.

Palmar: Pertaining to the palm side of the hand.

Dorsal: Pertaining to the upper side or back of the hand.

Radial: Pertaining to the thumb side of the hand.

Ulnar: Pertaining to the side of the hand opposite the thumb side.

Phalanx: Any of the individual bones within a finger or thumb.

Metacarpal: The third bone from the tip (distal phalanx) of the thumb, and the fourth bone from the tip (distal phalanx) of the fingers.

Proximal phalanx: The bone directly distal to the metacarpal of any finger or thumb.

Middle or intermediate phalanx: The bone positioned between the distal phalanx and proximal phalanx of any finger, the thumb having no middle phalanx.

Distal phalanx: The most distal bone of any finger or thumb, e.g. the bone that is referred to as the tip of the finger or tip of the thumb.

The presently disclosed adaptive device 10 and storage device 70 for the interchangeable implement member 36 help provide increased independence and autonomy for individuals that have mobility impairments or limitations, specifically those that are unable to grasp or unable to retain a grasp on objects. The adaptive device 10 and storage device 70 and uses thereof can be used by an individual with mobility impairments or mobility limitations without the assistance of an additional person.

Figure 1A:
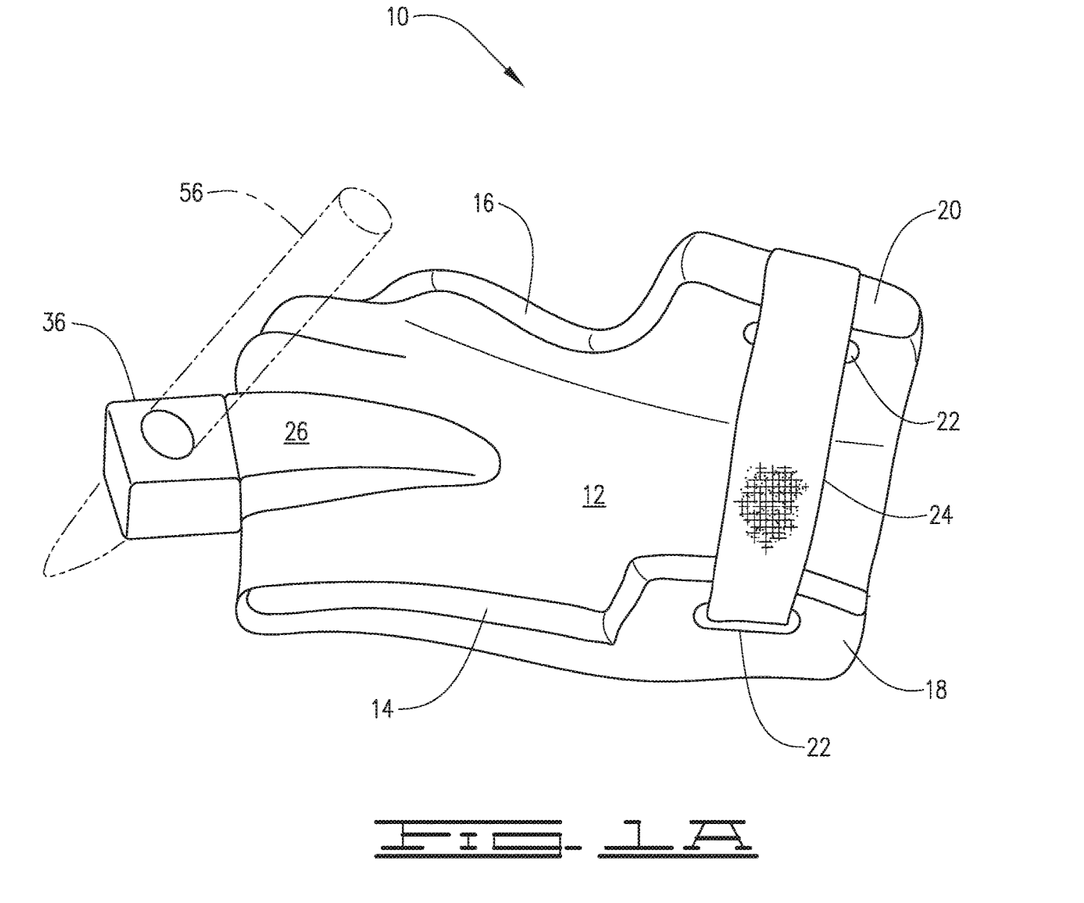
FIG. 1A is a view of the adaptive device.
Figure 1B:
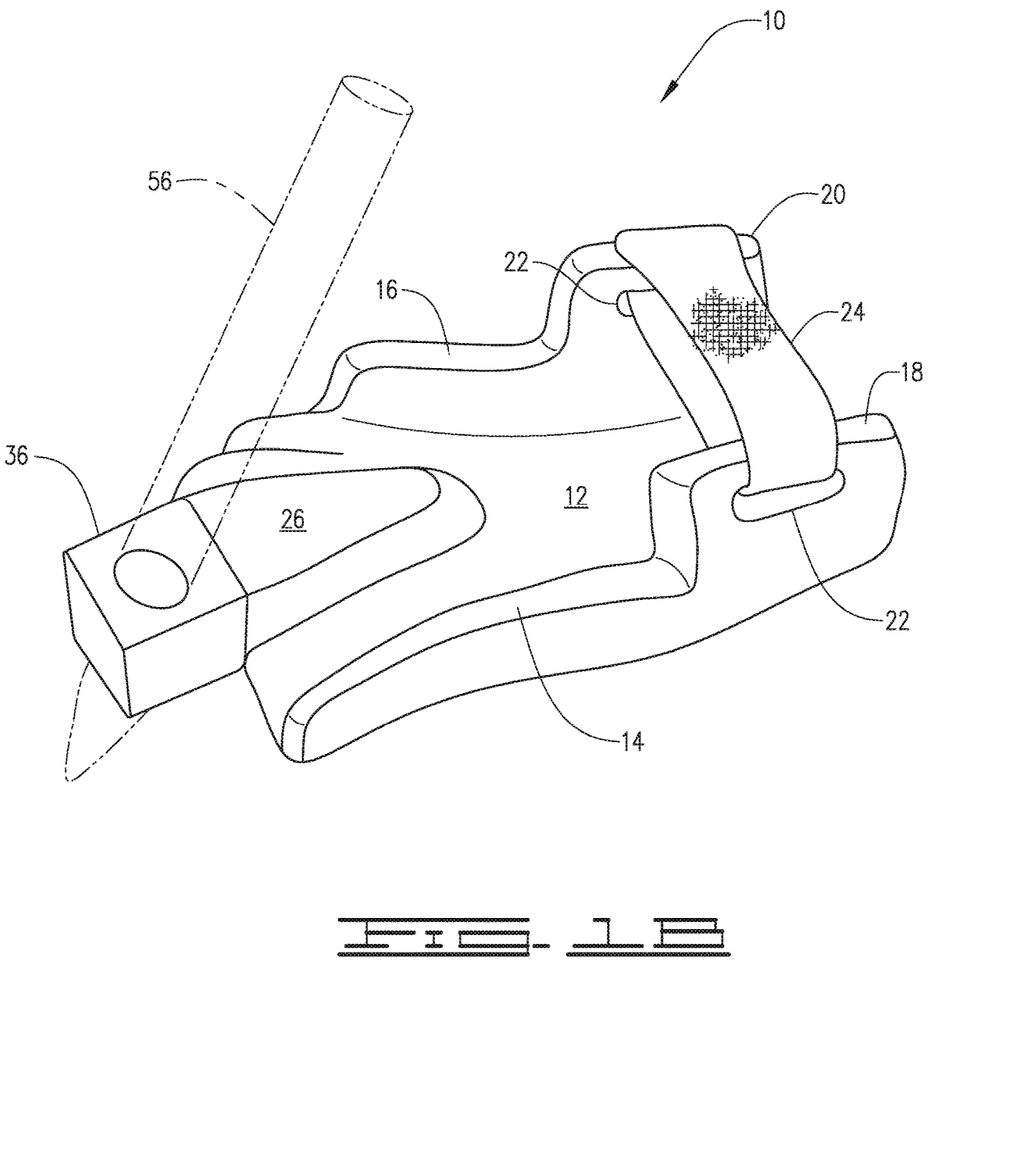
FIG. 1B is another view of the adaptive device.

With reference to FIGS. 1A and 1B, adaptive device 10 is for a hand 8 of a user having a mobility impairment. Adaptive device 10 supports a hand of a user in a relaxed and ergonomic position. Adaptive device includes body 12. Body 12 has a proximal end and a distal end, and supports a palm and a wrist when worn by a user.

Optionally, the length of the adaptive device 10 may be such that it supports only the palm of a hand, the palm and the wrist, the palm and a partial portion of the wrist, or support the palm, wrist, and extend proximally up the forearm of a user. Body 12 may also extend to support a portion of some or all of the fingers of the user.

For example, as depicted in the FIGS. 1A-2B, body 12 extends in the distal direction a length sufficient to support the thumb at or distal to the proximal phalanx. The thumb is supported in a generally relaxed position. As depicted, body 12 also extends in the distal direction a length sufficient to support the remaining phalanges, ending at or past the metacarpal bones or middle phalanges with respect to each phalanx. The phalanges are supported in a generally relaxed position.

Figure 2A:
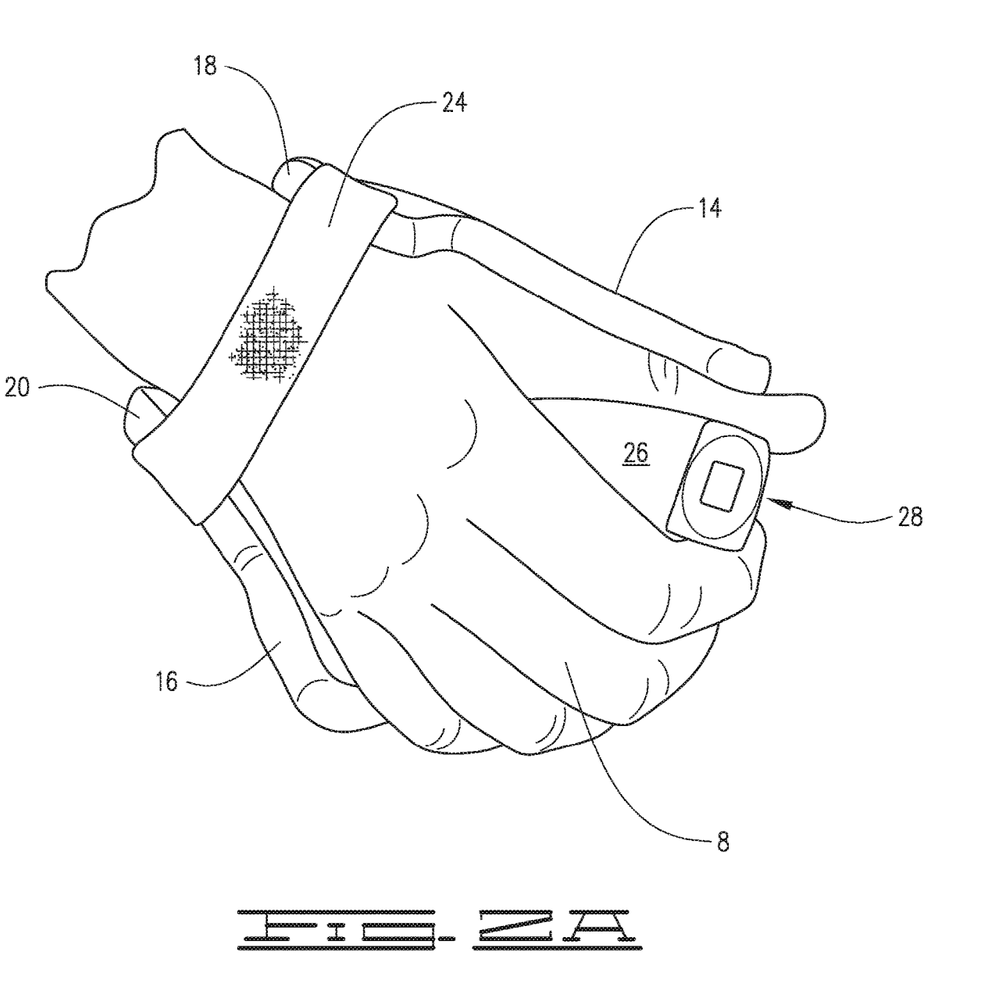
FIG. 2A is an angled view of the top of the adaptive device illustrating hand placement.
Figure 2B:
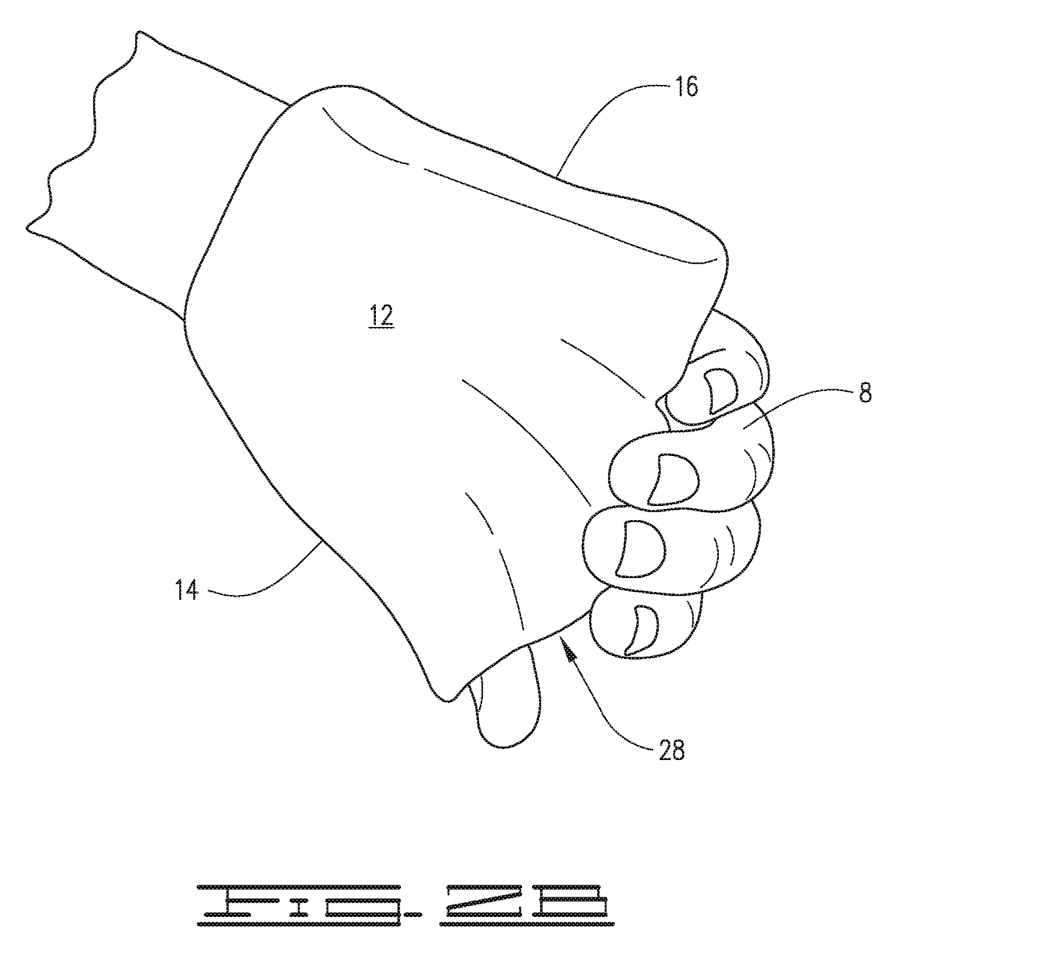
FIG. 2B is a bottom view of FIG. 2A.

The length and shape of body 12 is contoured to correspond with and conform with the shape of respective anatomy of the user for which body 12 will be in contact with. Body 12 is provided with suitable length and width to correspond to the dimensions of the average hand, further details regarding the size and material characteristics of adaptive device 10 are provided below. In use, body 12 is positioned under the palm of a hand. As shown in FIG. 2B, the bottom exterior surface of body 12 is substantially planar.

Adaptive device 10 includes two sidewalls 14 and 16 extending upward from body 12. Sidewalls 14 and 16 are oppositely disposed and laterally extending the length of body 12. Sidewalls 14 and 16 are separated from one another by body 12 and the area defined by sidewalls 14 and 16 and body 12 accommodate the palm of a user.

As shown in the figures, sidewalls 14 and 16 extend up the radial and ulnar sides of the hand. The height of sidewalls 14 and 16 do not need to be the same height as each other. The height of sidewalls 14 and 16 can vary along the length of body 12, e.g. gradually slope or include a step, depending upon the portion of the hand of the user and the corresponding portion of sidewalls 14 and 16. The height of sidewalls 14 and 16 may vary along its length as sidewalls 14 and 16 are to set a boundary for receiving the hand of a user within adaptive device 10.

For example, as shown in FIG. 1B, a forward portion of sidewall 16 gradually slopes downward toward the distal end of body 12 for ergonomic placement and support of the user's hand.

With reference to FIGS. 1A and 1B, a proximal end of each sidewall 14 and 16 (and proximal end of body 12), each sidewall 14 and 16 includes a slot 22 for receiving a securing member 24. Slots 22 are positioned opposite from each other on their respective sidewall 14 and 16. As shown in the figures, adaptive device 10, may include a portion of sidewall 14 and 16 with the slot 22 is greater in height (designated as reference numerals 18 and 20) than a forward or distal portion of sidewall 14 and 16. Elevated sidewall portions 18 and 20 are proximally positioned along body 12 and form a partial cuff.

Securing member 24 is received within slot 22 of sidewalls 16 and 14. Securing member 24 removably secures hand 8 with adaptive device 10 when worn by the user. With reference to FIGS. 1A, 1B, and 2A, securing member 24 is attached to adaptive device 10, for instance, by positioning a strap between slots 22 of each sidewall 14 and 16. The user can adjust the strap per the user's preference to secure the user's hand between the strap and body 12 of adaptive device 10. Coupling and adjustment of securing member 24 may be done with the assistance of another person or without assistance with the user using his/her hand or teeth or both.

Securing member 24 is adjustable, lightweight, and made of durable material such as one or more strappings made of hook and loop fastener, elastic, leather, or neoprene. Securing member 24 may be made of comfortable or cushioned material or include a cushion member (described below) thereon to prevent blisters, sores, or other afflictions as a result of friction between the securing member 24 and hand 8. Securing member 24 may include press-fitted buttons or other fasteners that enable removable coupling between the hand of a user and adaptive device 10.

Securing member may also have a terminal end of strap anchored through slot 22 of one of the sidewalls and then guided through and around the opposite slot 22. Securing member 24 may be permanently affixed to adaptive device 10 by, for instance, sewing (using slot 22 to loop strap through and sewing the strap to itself) or using an adhesive. Securing member 24 may be removably affixed to adaptive device 10 as previously described with reference to FIGS. 1A, 1B, and 2A. Securing member 24 may also include a snap assembly, a plurality of either the male or female member on a terminal end of securing member 24. The other complementary member of the snap assembly is attached to the adaptive device 10. The two members the snap assembly can be snapped together to secure the user's hand with adaptive device 10.

Adaptive device 10 may also include an additional securing member 24 (not depicted) that that is distal on body 12 of adaptive device 10, i.e., positioned closer to the distal portion of a user's metacarpals. This additional securing member can be similarly arranged and secured to adaptive device 10 as described above.

Adaptive device 10 may include a plurality of securing members and corresponding voids within adaptive device 10 for securing adaptive device with a hand of a user.

The above mechanisms are merely illustrative of the possibilities for attaching securing member 24 with adaptive device 10 and for securing adaptive device 10 to the hand of a user. Many other mechanisms could be used and are within the scope of the present disclosure.

For example, in use, hand 8 is placed in the space defined sidewalls 14 and 16 and on top of body 12. Securing member 24 may be pre-positioned within slots 22 and the user slides his/her hand under securing member 24 into adaptive device 10 and thereafter adjust securing member 24 to the user's preference. Securing member 24 may be secured to adaptive device 10 after the user positions his/her hand and then adjusted per user preference. Sidewalls 14 and 16 may slightly bend or flex when securing member 24 is tightened. Generally, as will be further described below, sidewalls 14 and 16 and body 12 comprise a durable and rigid material.

The surfaces of adaptive device 10 in contact with the user can optionally be lined with a cushion member (not depicted). The cushion member may be positioned on top of body 12 and/or along the inward facing surfaces of sidewalls 14 and 16. Cushion member comprises a pliable material and may be foam, cloth, or other suitable material to prevent blisters, sores, or other afflictions as a result of friction. The cushion member can cover the entire surface of body 12 and inward facing surfaces of sidewalls 14 and 16 or be selectively positioned on such surfaces per the user's preference. Cushion member may also be comprised of material to absorb moisture from the user. Cushion member may be temporarily placed and/or secured to adaptive device 10 or may be permanently affixed to adaptive device 10. Cushion member is thin so as not to interfere with the overall fit or comfort of adaptive device 10 when worn by a user.

Adaptive device 10 includes retention member 26 positioned on the body at the distal end thereof. Retention member 26 provides a separation between an index finger and a thumb of hand 8 of a user, as shown in FIG. 2A. Retention member 26 removably couples with an interchangeable implement member 36.

As shown in FIGS. 1A and 2A retention member 26 is positioned on body 12 in the purlicue area of a hand, the space (or crook) between the index finger and thumb, and provides a separation between an index finger and a thumb of the hand of a user. The figures depict retention member 26 occupying a substantial portion of the purlicue area. Other positions of retention member 26 within the purlicue area of a hand are also suitable, e.g. not occupying as much space as depicted in the figures.

Retention member 26 may be made of the same material as body 12 or may be made of a material that is a less thermosensitive plastic material than body 12. Retention member 26 may be made or molded as a unitary structure with body 12 or may be secured to body 12 via adhesives and/or fasteners.

With reference to FIGS. 3A-3E, retention member 26 includes an opening 28 at a distal end of the retention member 26 for removable coupling with the interchangeable implement member 36.

Figure 3B:
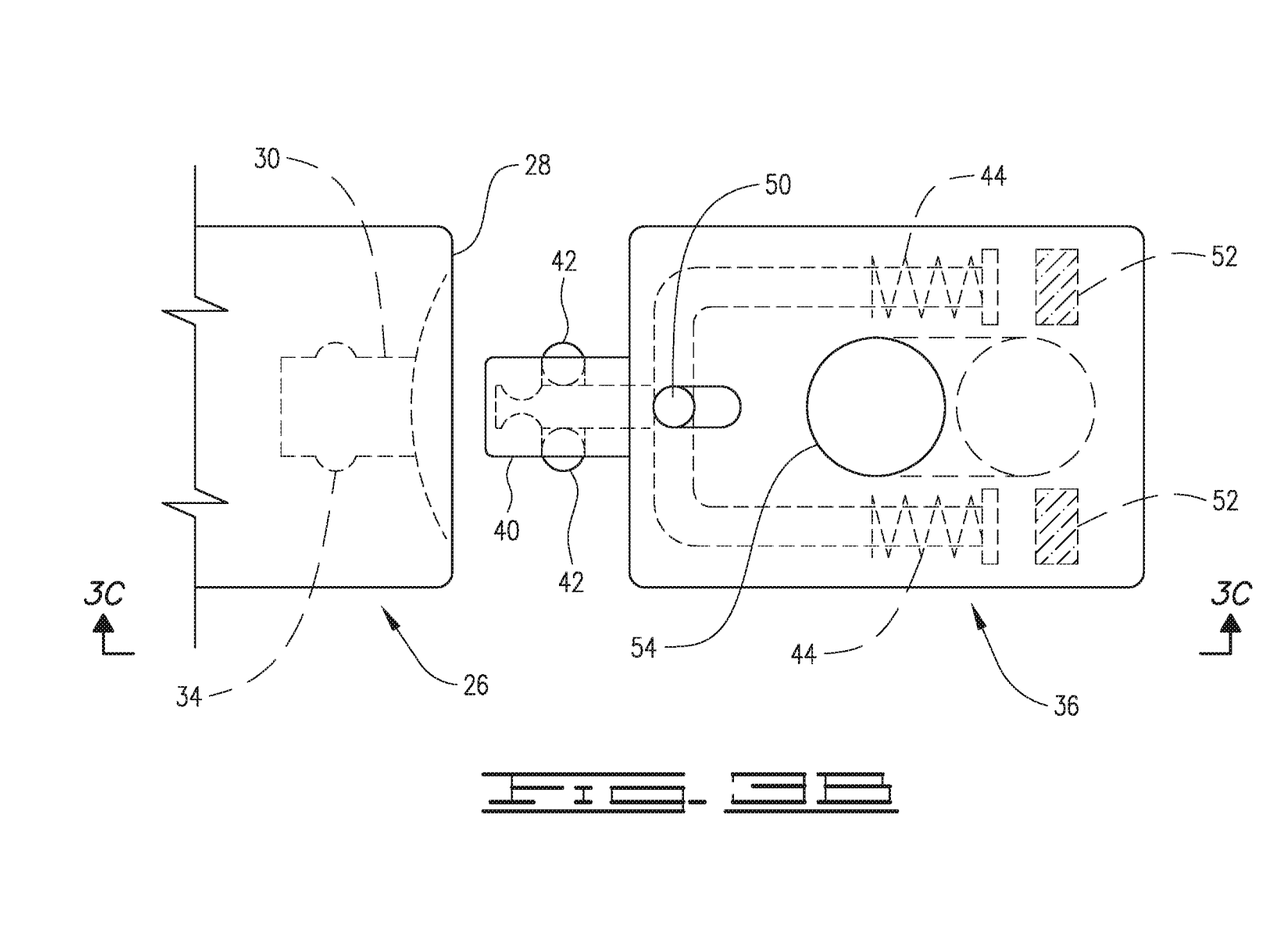
FIG. 3B is a top view of the interchangeable implement member and retention member of the adaptive device of FIG. 3A.

Retention member 26 has an inner cavity 30 with one or more outwardly projecting notches 34 or recesses 32 on the periphery of inner cavity 30 as depicted in FIGS. 3B, 3D, and 3E. As will be further described below, inner cavity 30 receives connection member 40 of the interchangeable implement member 36. Notches 34 receives balls 42 protruding from connection member 40, and recesses 32 receive enlarged heads 43 of flexible arms 41 to provide removable coupling of retention member 26 with interchangeable implement member 36. Opening 28 may be contoured to help guide connection member 40 to inner cavity 30 of retention member 26.

Although depicted has having two notches 34 or two recesses 32 to correspond with two balls 42 or two enlarged heads 43, respectively, retention member 26 may have a single notch 34 or single recess 32 or more than two notches 34 or more than two recesses 32; similarly, connection member 40 can have a similar number of balls 42 or enlarged heads 43 to correspond to notch(es) 34 or recess(es) 32, respectively.

Inner cavity of retention member may be any length to sufficiently secure and retain interchangeable implement member 36 and enable effective use of implement 56 of interchangeable implement member 36 by a user. Non-limiting lengths for inner cavity 30 of retention member 26 can range from 0.5 inches to 1.5 inches, 0.5 inches to 1.0 inches, 0.5 inches to 0.75 inches, or 0.75 inches in length.

Interchangeable implement member 36 is shown in FIGS. 1A, 1B, and 3A-3E. Interchangeable implement member 36 comprises a housing 38 and a connection member 40 protruding from a proximal end of the interchangeable implement member 36. As will be discussed below, the connection member 40 is received by and removably coupled to the retention member 26.

Interchangeable implement member 36 carries an implement 56 for use by the individual with a mobility impairment. For example, interchangeable implement member 36 carries a writing implement, a grooming implement, an entertainment implement, a hygienic implement, an eating utensil implement, or a cooking implement. Non-limiting examples of the foregoing include, pens, pencils, paint brushes, crayons, markers, combs, hairbrushes, razors, toothbrushes, floss, page turner, spoon, fork, knife, cooking utensils, etc. Any object that can be removably attached to adaptive device 10 as described in the present disclosure is suitable.

Interchangeable implement member 36 has a void 54 passing through housing 38 between a top and bottom surface of interchangeable implement member 36. An implement 56 is positioned within void 54 for utilization by the user. Implement 56 can be manufactured to be permanently carried by interchangeable implement member 36 such that a user will change out the entire interchangeable implement member 36 depending upon the desired activity of the user. Interchangeable implement member 36 may be produced without implement 56 carried thereby and simply have void 54 defining a passageway therethrough and allow for a user to insert and secure his/her desired implement through interchangeable implement member 36.

FIG. 3C depicts void 54 in housing 38 as angled. Void 54 may be angled anywhere from about 30 degrees to about 90 degrees relative to the top surface of housing 38. The angle of void 54 will depend upon the type of implement 56 carried by interchangeable implement member 36 to accommodate for various sizes, shapes, and end-uses of the specific implement 56. Housing 38 is a length sufficient to support the attachment of and use of various implements so that such implements may effectively be used for their respective purposes. Such a length may be adequate to support, for example, a pencil, in an ergonomic position and/or similar to the placement and positioning of implements by individuals without mobility impairments.

Connection member 40 is depicted in FIGS. 3A-3E. Connection member 40 is operably connected to a spring-loaded assembly 46 carried within the housing 38. With reference to FIGS. 3A-3D, spring-loaded assembly 46 includes a spring 44 positioned within the housing 38 and a ball 42 positioned within the connection member 40. As previously discussed, ball 42 is capable of protruding from and retracting into the connection member 40, e.g. similar to a ball plunger.

FIG. 3E illustrates another configuration of interchangeable implement member 36. With reference to FIG. 3E, connection member 40 includes a pair of compressible and flexible arms 41. An end of each arm 41 includes an outwardly facing enlarged head 43. Connection member 40 is operably connected to spring-loaded assembly 46 by flexible arms 41 of connection member 40. Spring-loaded assembly 46 includes a spring 44 positioned within housing 38 of connection member 40.

Spring-loaded assembly 46 includes a ferrous member 52 operably connected to spring 44 and, as depicted in FIG. 3D causes ball 42 to retract within connection member 40, or causes enlarged heads 43 to flex inward toward each other (not depicted) when the housing 38 is in proximity of a magnetic field sufficient to cause movement of spring-loaded assembly 46 or compression of spring 44 within housing 38. Alternatively, spring 44 may also be a magnetized spring in addition to ferrous member 52. Alternatively, spring 44 may be a magnetized spring and thus also be ferrous member 52. If spring 44 is a magnetized spring, it may be shielded in a manner so as to move in a compressive manner when a sufficient magnetic field is present from a specific direction so that interchangeable implement member 36 is unintentionally decoupled from retention member 26.

Interchangeable implement member 36 includes release lever 50 protruding from a surface of the interchangeable implement member 36. Release lever 50 is depicted as protruding from a top surface of interchangeable implement member 36, but release lever may also protrude from any other surface of interchangeable implement member 36 provided the general functionality of release lever 50 described herein is achieved. Release lever 50 may also be a button, slide, or any other similar mechanism that achieves the described functionality. Release lever 50 is operably connected to the spring-loaded assembly 46. With reference to FIGS. 3A-3D, when the release lever 50 is actuated, release lever 50 causes movement of spring-loaded assembly 46 or compression of the spring 44 and thereby cause ball 42 positioned within the connection member 40 to retract into the connection member 40. With reference to FIG. 3E, when the release lever 50 is actuated, release lever 50 causes movement of spring-loaded assembly 46 or compression of the spring 44 and thereby causes enlarged heads 43 to flex toward each other and thus move more centrally within inner cavity 30 to no longer be engaged within recesses 32.

With reference to FIGS. 3A-3D, interchangeable implement member 36 is removably secured to retention member 26. As connection member 40 of interchangeable implement member 36 is inserted through opening 28 and into inner cavity 30 of retention member 26, projecting balls 42 contact the interior surface of the retention member 26 and get pushed or urged inward within connection member 40 (and compress spring 44 of spring-loaded assembly 46). When connection member 40 is fully inserted within retention member 26, balls 42 within connection member 40 will be resiliently urged out and received within notches 34 on the periphery of inner cavity 30 to retain the interchangeable implement member 36 within retention member 26, thereby removably couple interchangeable implement member 36 and retention member 26 together.

With reference to FIG. 3E, interchangeable implement member 36 is removably secured to retention member 26. As connection member 40 of interchangeable implement member 36 is inserted through opening 28 and into inner cavity 30 of retention member 26, enlarged heads 43 contact the interior surface of the retention member 26 and get pushed or urged inward toward each other. When connection member 40 is fully inserted within retention member 26 (after enlarged heads 43 have passed their respective shoulder within inner cavity 30), enlarged heads 43 will be resiliently urged outward and received within recesses 32 within connection member 40 on the periphery of inner cavity 30 to retain the interchangeable implement member 36 within retention member 26, thereby removably couple interchangeable implement member 36 and retention member 26 together.

Adaptive device 10 has two methods to disengage retention member 26 and interchangeable implement member 36 from each other. A first method is through use of release lever 50 (as discussed above) and a second method is through use of magnetic field (as discussed briefly above). One option for disengagement involves storage device 70, which has a magnetic material thereon. Storage device 70 is described further below and will be described before describing the second method of disengagement retention member 26 and interchangeable implement member 36 from each other.

Components of adaptive device 10 are described above. Adaptive device 10 can be made various ways. For example, a bespoke body 12 and sidewalls 14 and 16 of adaptive device 10 may be made and customized to the hand of each particular user and retention member 26 can be positioned and affixed thereto by manually molding and forming body 12 and sidewalls 14 and 16 around the hand of a user. Another bespoke option is to 3D print body 12, sidewalls 14 and 16 based on a scan of the user's hand. Retention member 26 may also be 3D printed at the same time to form a unitary structure or may be attached separately to body 12. Body 12 and sidewalls 14 and 16 of adaptive device 10 may also be pre-molded and manufactured in multiple sizes based on the average hand size for youth and adults.

Regardless of the method of manufacture, adaptive device 10 may be made of a thermoplastic plastic material or thermoset plastic material that is safe for contact with human skin and that is firm, durable, and can withstand impact to avoid, for example, permanent deformation (bending, warping, breaking) of adaptive device 10 during typical use and operation. The thermoplastic material can be semi-moldable through use of an external heating element, such as a hair dryer, heat gun, or the like, to provide adjustments to tailor adaptive device 10 to the hand of the specific user. The temperature at which the thermoplastic material becomes moldable is higher than the body temperature of a user. An example of a suitable thermoplastic material includes but is not limited to polycaprolactone.

In most applications of the described adaptive device 10 and storage device 70, the selected material comprising adaptive device 10 and storage device 70 and components thereof will be generally safe for use in connection with direct human skin contact and other than ordinary wear and tear will not be susceptible to erosion or wear due to environmental exposure.

Figure 4A:
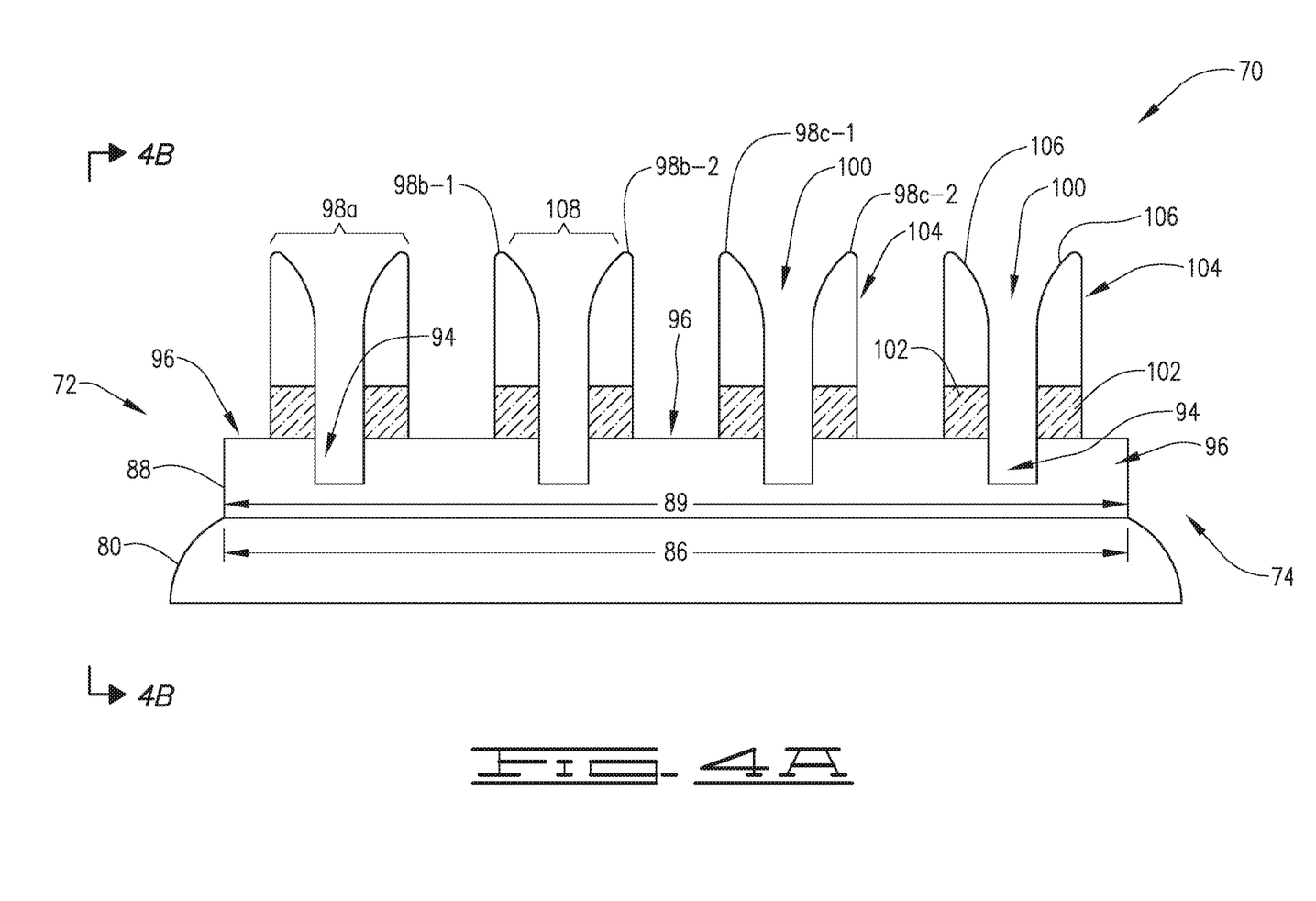
FIG. 4A is a front view of a storage device of an interchangeable implement member for the adaptive device.
Figure 4B:
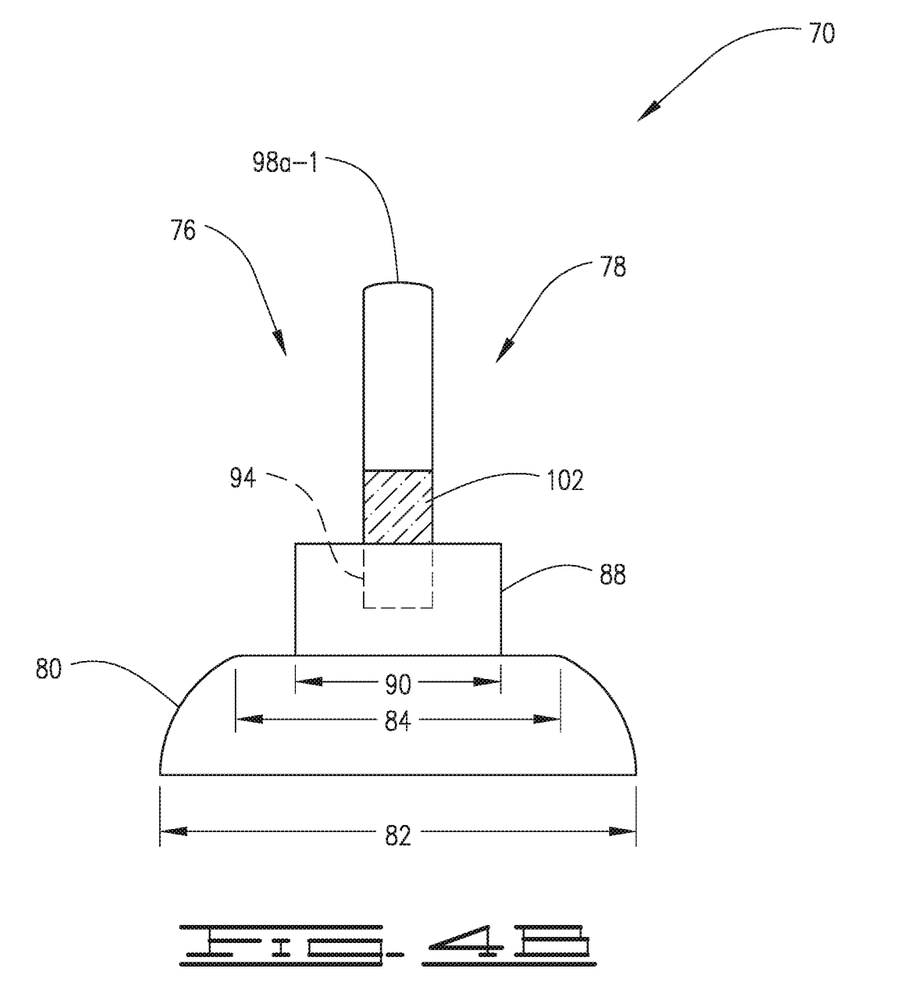
FIG. 4B is a side view of the storage device of the interchangeable implement member for the adaptive device of FIG. 4A.
Figure 5A:
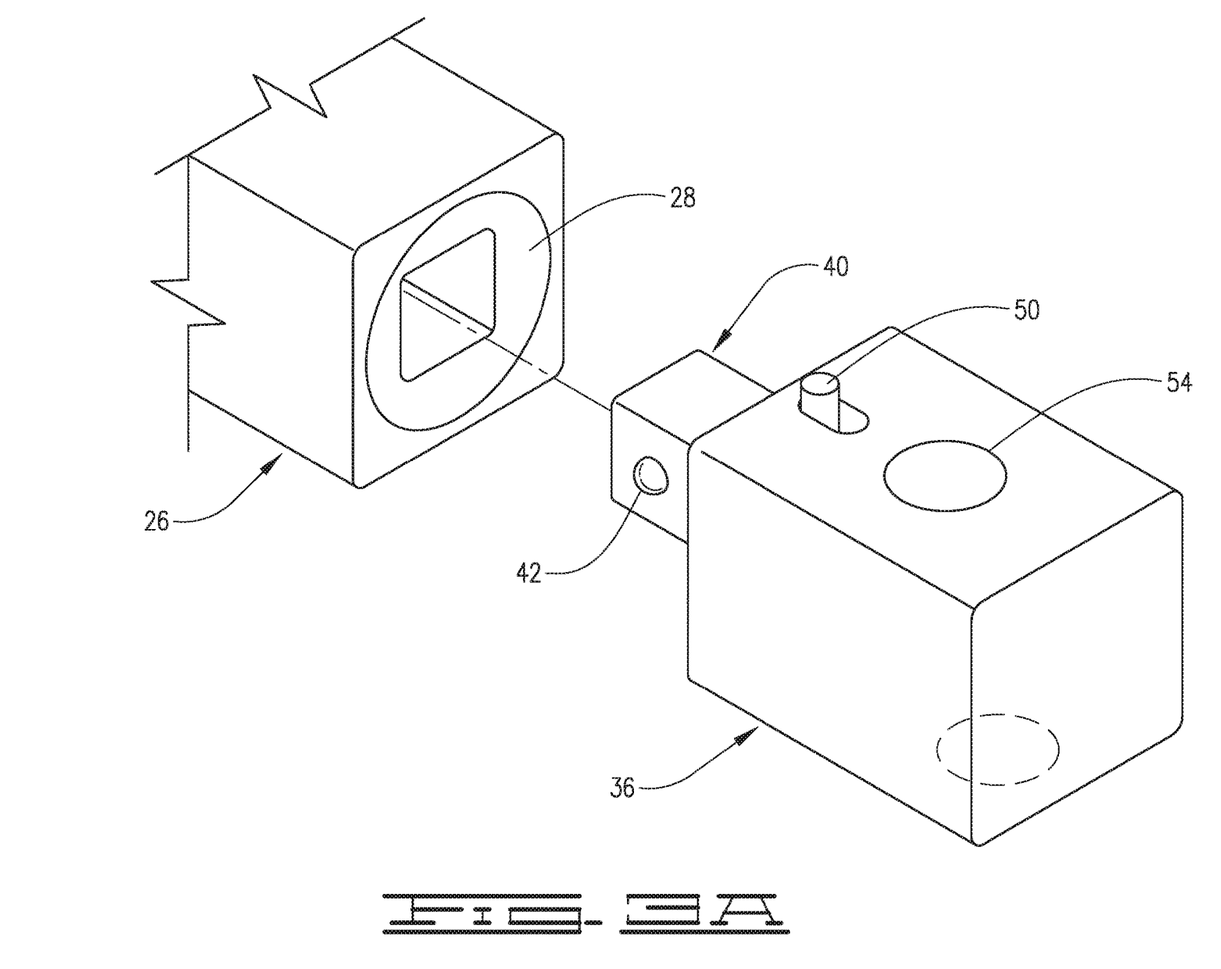
Figure 9:
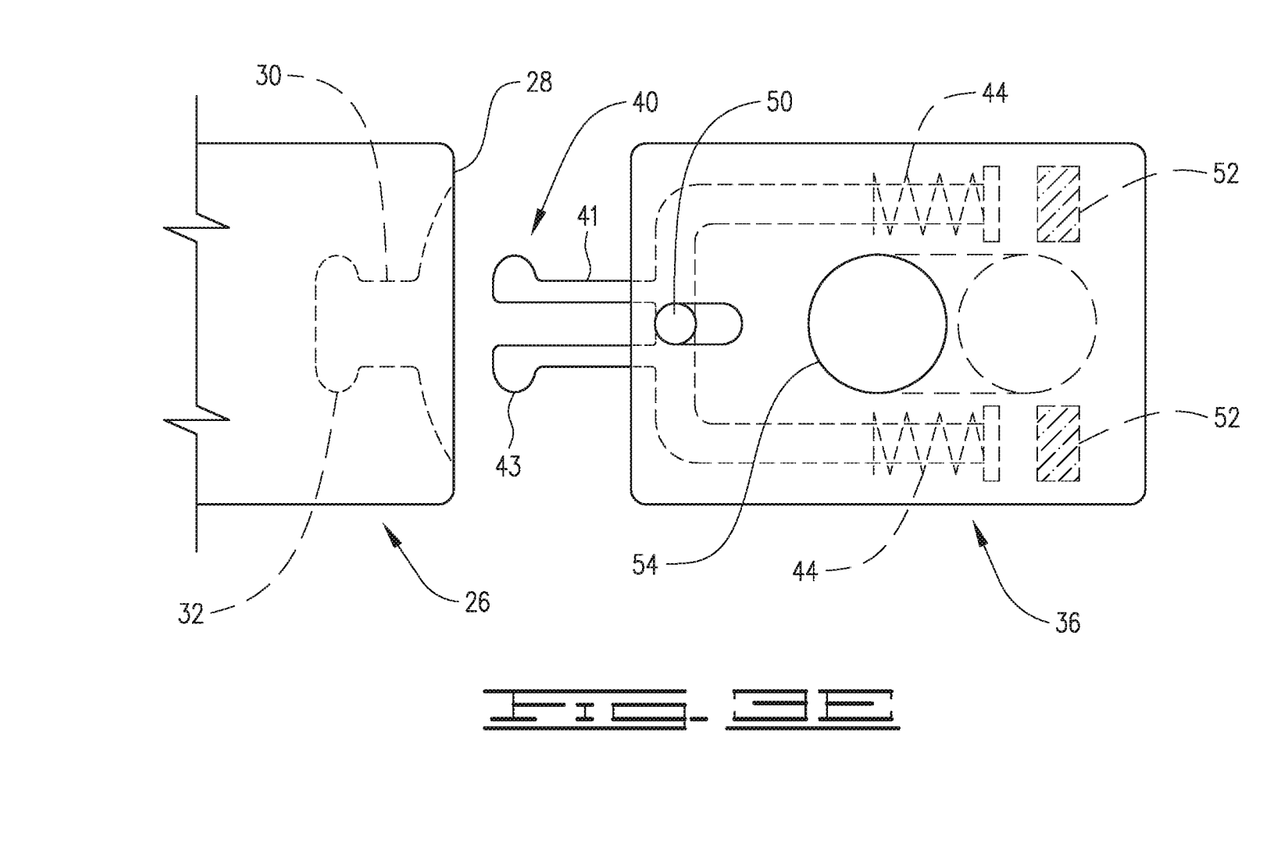

FIGS. 4A and 4B depict storage device 70. Storage device 70 holds one or more interchangeable implement members 36 for adaptive device 10. As will be discussed below, a user may use storage device 70 to aid in the attachment and removal of interchangeable implement member 36 from retention member 26 when a user is wearing adaptive device 10.

FIGS. 4A and 4B depict a front view and a side view, respectively, of storage device 70. FIGS. 4A and 4B are illustrative of a specific shape and configuration of storage device 70; however, storage device 70 is not limited to the depicted illustration.

Storage device 70 has a first end 72 and a second end 74 and a length defined between first end 72 and second end 74. Storage device 70 also includes a first side 76 and a second side 78 and a width defined between first side 76 and second side 78.

Storage device 70 comprises a base member 80. Base member 80 has a top surface and the top surface of base member has a width 84 and a length 86. The length 86 of the top surface of the base member is defined between a first end 72 and a second end 74 of the base member. The width 84 of the top surface of the base member defined between a first side 76 and a second side 78 of the base member. Base member 80 may be in the shape of a rectangular prism or a trapezoidal prism or other three-dimensional shape but with curved surfaces between a flat top surface and flat bottom surface where the top surface of base member 80 has a smaller length and width than the bottom surface of base member 80.

Base member 80 includes a non-skid or other friction element on the bottom to prevent displacement of storage device 70 in the event of an errant movement by the user, e.g. spasm. Base member 80 is also be weighted. Storage device 70 through base member 80 may also be affixed to the surface it is place on, e.g. clamped, screwed, nailed, or adhered with adhesive. Base member may be between about 2.0 inches to about 4.0 inches tall.

Storage device 70 includes a spacer member 88 positioned on top of the base member 80. Spacer member 88 has a crenellation top periphery of alternating crenels 94 and merlons 96 as depicted in FIG. 4A. Crenels 94 define a space to accommodate the implements 56 extending from any interchangeable implement members 36 positioned on storage device 70. The height of spacer member 88 as measured between its bottom surface and the top surface of a merlon 96 is about 4.0 inches.

As shown in FIGS. 4A and 4B, spacer member 88 has a width 90 defined between first side 76 and second side 78 of storage device 70 and a length 89 defined between first end 72 and second end 74 of storage device 70. As depicted in the figures, spacer member 88 has a width 90 less than the width 84 of the top surface of the base member and has a length 89 the same length 86 of the top surface of the base member. Spacer member 88 is depicted as centrally positioned on the top surface of base member 80. As shown in the figures, spacer member 88 is positioned on a top surface of the base member 80 and an edge of a first side or a second side of the spacer member is not aligned with an edge of a first side of the top surface of the base member or a second side of the top surface of the base member. Although the figures depict the first end and second ends of spacer member 88 and the top surface of base member 80 in substantial alignment, the length of spacer member 88 may be such that it is not the same length of base member 80.

While the figures depict the midline of the widths of spacer member and of the top surface of base member being aligned, the two may be positioned with respect to each other in a number of configurations. For example, in another arrangement spacer member 88 is positioned on a top surface of the base member and an edge of a first side or a second side of the spacer member is substantially aligned with an edge of a first side of the top surface of the base member or a second side of the top surface of the base member. For example, a width of spacer member 88 may be the same as the width 84 of the top surface of base member 80.

Storage device 70 includes a plurality of guiderails, wherein each guiderail 98a-1, 98a-2, is positioned adjacent to a crenel 94 and on top of a merlon 96 and emanates upward from the top periphery of the spacer member 88. Guiderails positioned on opposite sides of a shared crenel 94 are a guiderail pair 98a, 98b, 98c, and a passage 100 is defined between each guiderail 98b-1, 98b-2, in the guiderail pair 98b of the shared crenel 94. Passage 100 receives housing 38 of interchangeable implement member 36 and connection member 40 projects from either the first side 76 or second side 78 of storage device 70 depending upon the orientation of interchangeable implement member 36. Guiderails are approximately 8.0 inches in height.

A lower portion 102 of each of the plurality of guiderails is magnetic. For example, the bottom two inches of each guiderail is magnetic. For example, lower portion 102 may include a magnetic material thereon. For example, the lower portion 102 may be a thin magnet wrapped around and affixed to each individual guiderail.

An upper portion 104 of each of the plurality of guiderails (above the lower portion 102) and is not magnetic or does not have a magnetic material thereon, has an angled surface 106. Each guiderail per guiderail pair 98a is positioned with its angled surface 106 toward its shared crenel 94. Where guiderails have angled surface 106, a wide opening 108 is defined therebetween which funnels down toward and guides the user into passage 100.

For example, when a user is wearing adaptive device 10 and an interchangeable implement member 36 is positioned and stored between two guiderails of a guiderail pair 98a and a user desires to attach the interchangeable implement member 36 with retention member 26 the user will take the following steps. When interchangeable implement member 36 is positioned within storage device 70, the magnetic lower portion 102 is of sufficient strength to cause balls 42 to retract within connection member 40 as depicted if FIG. 3D. A user will bring their hand to connection member 40 and present open end 28 of retention member 26 to connection member 40 to insert connection member 40 into retention member 26. Once in position, the user will move his/her hand upward toward opening 108. Once the user moves housing 38 a sufficient distance away from magnetic lower portion 102, spring 44 will return to its starting position and urge balls 42 outward to be received within notches 34 of retention member 26 and thereby secure interchangeable implement member 36 with retention member 26. If connection member 40 includes flexible arms 41 as depicted in FIG. 3E, once the user moves housing 38 a sufficient distance away from magnetic lower portion 102, spring 44 will return to its starting position and urge enlarged heads 43 (and flexible arms 41) outward for enlarged heads 43 to be received within recesses 32 of retention member 26 and thereby secure interchangeable implement member 36 with retention member 26. Disengagement of retention member 26 and interchangeable implement member 36 using storage device 70 is the reverse of the above-described engagements.

To decouple interchangeable implement member 36 from retention member 26 using storage device 70, the user places interchangeable implement member 36 through opening 108 of a guiderail pair and moves his/her hand downward in the direction of passage 100. When the magnetic field from lower portion 102 causes balls 42 to retract (or enlarged heads 43 of flexible arms 41 to flex inward toward each other), the user will pull his/her hand away from storage device 70.

Storage device 70 aids the user to attach and detach interchangeable implement member 36 without the assistance of an additional person.

Storage device 70 may be made of different components affixed together for form a single integral structure. Storage device 70 may be made such that it is a unitary structure. Like adaptive device, storage device 70 is made of any material(s) that is safe for contact with human skin. Storage device 70 is also made of material(s) that are durable and can withstand impact to avoid, for example, permanent deformation (bending, warping, and/or breaking) of storage device 70 during typical use and operation.

Although certain steps are described herein and illustrated in the figures as occurring sequentially, some steps may occur simultaneously with each other or in an order that is not depicted. The present disclosure of the described apparatuses, devices, uses, methods, techniques, functions, and products produced therefrom are not to be limited to the precise descriptions and illustrations. Other embodiments and variations will be apparent to one skilled in the art. As such, the foregoing description merely enables and describes the general apparatuses, devices, products, uses, methods, techniques, functions, and products produced therefrom disclosed herein. While certain embodiments have been described for the purpose of this disclosure, those skilled in the art can make changes without departing from the spirit and scope thereof. Thus, the appended claims define what is claimed.

What is claimed is:

1. An adaptive device for a hand comprising:
   a body;
      wherein the body has a proximal end and a distal end, and
      wherein the body supports a palm and a wrist when worn by a user,
   two sidewalls extending upward from the body and on opposite sides of the body from each other;
      wherein at a proximal end of each sidewall, each sidewall includes a slot for receiving a securing member,
      wherein the securing member removably secures the hand with the adaptive device when worn by the user, and
   a retention member positioned on the body at the distal end and the retention member provides a separation between an index finger and a thumb of the hand, and the retention member removably couples with an interchangeable implement member; wherein the interchangeable implement member comprises a housing, and a connection member protruding from a proximal end of the interchangeable implement member, the connection member is received by and removably coupled to the retention member; and wherein the connection member is operably connected to a spring-loaded assembly carried within the housing, the spring-loaded assembly includes a spring positioned within the housing and a ball positioned within the connection member and the ball capable of protruding from and retracting into the connection member.

2. The adaptive device of claim 1, wherein the retention member includes an opening at a distal end of the retention member for removably coupling with the interchangeable implement member.

3. The adaptive device of claim 1, wherein the spring-loaded assembly includes a ferrous member operably connected to the spring and causes the ball to retract within connection member when the housing is in proximity of a magnetic field sufficient to cause compression of the spring.

4. The adaptive device of claim 1, wherein the retention member includes an opening at a distal end of the retention member and has an inner cavity with a notch, wherein the inner cavity receives the connection member of the interchangeable implement member and the notch receives the ball protruding from the connection member to removably couple with interchangeable implement member.

5. The adaptive device of claim 1, wherein the housing defines a void for carrying an implement.

6. The adaptive device of claim 1, wherein the interchangeable implement member carries a writing implement, a grooming implement, an entertainment implement, a hygienic implement, an eating utensil implement, or a cooking implement.

7. The adaptive device of claim 1, further comprising a cushion member positioned on top of the body, the cushion member comprising a pliable material.

8. The adaptive device of claim 1, further comprising a release lever protruding from a surface of the interchangeable implement member and operably connected to the spring-loaded assembly and when the release lever is actuated the release lever causes compression of the spring and thereby causes the ball positioned within the connection member to retract into the connection member.

9. The adaptive device of claim 1, wherein the adaptive device is made of a thermoplastic material.

10. An adaptive device for a hand comprising:
    a body;
       wherein the body has a proximal end and a distal end, and
       wherein the body supports a palm and a wrist when worn by a user,
    two sidewalls extending upward from the body and on opposite sides of the body from each other;
       wherein at a proximal end of each sidewall, each sidewall includes a slot for receiving a securing member,
       wherein the securing member removably secures the hand with the adaptive device when worn by the user, and
    a retention member positioned on the body at the distal end and the retention member provides a separation between an index finger and a thumb of the hand, and the retention member removably couples with an interchangeable implement member; wherein the interchangeable implement member comprises a housing, and a connection member protruding from a proximal end of the interchangeable implement member, the connection member is received by and removably coupled to the retention member; and wherein the connection member includes a pair of flexible arms and an end of each arm includes outwardly facing enlarged heads and wherein the connection member is operably connected to a spring-loaded assembly carried within the housing.

11. The adaptive device of claim 10, wherein the retention member includes an opening at a distal end of the retention member for removably coupling with the interchangeable implement member.

12. The adaptive device of claim 10, wherein the housing defines a void for carrying an implement.

13. The adaptive device of claim 10, wherein the interchangeable implement member carries a writing implement, a grooming implement, an entertainment implement, a hygienic implement, an eating utensil implement, or a cooking implement.

14. The adaptive device of claim 10, further comprising a cushion member positioned on top of the body, the cushion member comprising a pliable material.

15. The adaptive device of claim 10, wherein the adaptive device is made of a thermoplastic material.

16. The adaptive device of claim 10, wherein the spring-loaded assembly includes a spring and a ferrous member operably connected to each other and wherein the spring is operably connected to the pair of flexible arms of the connection member, and wherein the spring-loaded assembly causes the enlarged heads of connection member to flex toward each other when the housing is in proximity of a magnetic field sufficient to cause compression of the spring.

17. The adaptive device of claim 10, wherein the retention member includes an opening at a distal end of the retention member and has an inner cavity with two oppositely positioned recesses on inner cavity's periphery, wherein the inner cavity receives the connection member of the interchangeable implement member and each recess receives the enlarged head of the flexible arms of connection member to removably couple with interchangeable implement member.

18. The adaptive device of claim 10, further comprising a release lever protruding from a surface of the interchangeable implement member and operably connected to the spring-loaded assembly and when the release lever is actuated, the release lever causes compression of the spring and thereby causes the enlarged heads of connection member to flex toward each other.

* * * * *